United States Patent [19]
Lin et al.

[11] Patent Number: 5,863,882
[45] Date of Patent: Jan. 26, 1999

[54] CLEANER AND SANITIZER FORMULATION

[75] Inventors: Jian-Er Lin, Roanoke, Va.; Douglas A. Dent, New Hope, Pa.

[73] Assignee: Sybron Chemical Holdings, Inc., Wilmington, Del.

[21] Appl. No.: 941,417

[22] Filed: Sep. 30, 1997

Related U.S. Application Data

[63] Continuation-in-part of Ser. No. 585,912, Jan. 16, 1996, abandoned.

[51] Int. Cl.$^6$ .............................. C11D 3/00; D06M 16/00
[52] U.S. Cl. ......................... 510/397; 435/247; 435/264; 510/191; 510/195; 510/397; 510/422; 510/424
[58] Field of Search ...................... 510/191, 195, 510/393, 397, 421, 422, 424, 247, 260, 264

[56] References Cited

U.S. PATENT DOCUMENTS

| | | | |
|---|---|---|---|
| 4,252,663 | 2/1981 | Eriksson | 510/341 X |
| 4,347,153 | 8/1982 | Hooper et al. | 510/102 |
| 4,655,794 | 4/1987 | Richardson et al. | |
| 4,752,563 | 6/1988 | Kortright et al. | |
| 4,861,514 | 8/1989 | Hutchings | 510/102 |
| 4,959,303 | 9/1990 | Milburn et al. | |
| 4,959,304 | 9/1990 | Simonson | |
| 5,179,001 | 1/1993 | Young et al. | |
| 5,179,018 | 1/1993 | Bogard, Jr. | |
| 5,187,061 | 2/1993 | Gutterson et al. | |
| 5,192,678 | 3/1993 | Iwami et al. | |
| 5,449,619 | 9/1995 | Griffin et al. | |

FOREIGN PATENT DOCUMENTS

| | | |
|---|---|---|
| 0569140 | 11/1993 | European Pat. Off. |
| 06092806 | 4/1994 | Japan |

*Primary Examiner*—Margaret Einsmann
*Attorney, Agent, or Firm*—Wall Marjama & Bilinski

[57] ABSTRACT

The formulations of the invention comprise a suspension of a sanitizing composition, bacterial spores, surfactants, a thickening agent, and abrasive particles all contained in aqueous solution. These formulations can be used for cleaning and sanitizing bathroom fixtures, sinks, toilet bowls, and other dirty and contaminated surfaces, and have the advantages of being a good surface cleaning agent and a good sanitizer along with providing the long term effect of beneficial bacteria that control pathogens and degrade wastes both on the surface and in the sewage system associated with the surface being treated.

10 Claims, 4 Drawing Sheets

Growth of P. aeruginosa PRD 10 with and without vegetative cells of mixed B. amyloliquefaciens, B. pasteurii, and B. laevolacticus (1:10 dilutued plate count broth, initial cell conc.: PRD 10=$10^4$, veg. cell = $10^6$)

Spore shelf-stability of the formula 5,863,882

CLEANER AND SANITIZER FORMULATION

This application is a continuation-in-part of application Ser. No. 08/585,912, filed Jan. 16, 1996, now abandoned.

FIELD OF THE INVENTION

This invention is directed to novel formulations or compositions which are suitable for cleaning and sanitizing bathroom fixtures, sinks, toilet bowls, and other dirty and contaminated surfaces.

BACKGROUND OF THE INVENTION

Surface cleaners containing surfactants, both with and without abrasive, have long been utilized for removing soils, dirt, dried urine, stubborn stains, deposit, and scum from fixtures, sinks, toilet bowls, and other fixtures. These products are particularly useful in cleaning toilets, sinks, and other surfaces that are then rinsed with water and discharged to the sewage collection systems, holding tanks, or septic systems.

In association with surface cleaning, sanitization of surfaces is also desirable. By inactivating or reducing pathogens, chances for disease transmission due to indirect contacts can be eliminated or decreased. Most of the recently available sanitizing or disinfecting products contain chemicals such as hypochlorites, quaternary ammonium compounds, pine oil, etc.

Almost universally, the surface cleaning and sanitizing products are highly alkaline or acidic and use of these products causes potential damage to beneficial microorganisms in the collection lines, septic systems, or holding tanks. In many applications, inhibition of beneficial microbial activity is clearly a disadvantage. Furthermore, most of the available surface cleaning and sanitizing products are corrosive to materials (particularly metals) used to construct restroom fixtures. Some of the major sanitizing agents, such as hypochlorites, form chlorinated hydrocarbons, which are toxic to human beings, detrimental to the environment, and difficult to biodegrade.

It has been recently suggested that nonpathogenic microbes be used to inhibit pathogenic organisms (G. Haas, ASM News, June, 1995). The nonpathogenic microbes would be applied to locations where pathogens are present to inhibit the pathogens. The mechanisms involved are substrate competition, production of antibiotics, etc. When chemicals are used for sanitization, they kill the pathogens only during application or for a short time thereafter. In contrast, microbes, such as the beneficial microbes of this invention, can have effects on preventing the growth of pathogens over the long term. In addition, the beneficial microbes of this invention seed the connecting drain lines and waste collection and treatment systems, and enhance the degradation of organic wastes.

An objective of the present invention is to provide a formulation which has strong surface cleaning and sanitizing properties without being highly alkaline, acidic, corrosive or detrimental to the environment. A further objective of the invention is to provide a formulation that contains a microbial component that: 1) provides long-term protection against the colonization of surfaces and sewage systems by pathogenic organisms, and 2) enhances biodegradation of organic wastes.

SUMMARY OF THE INVENTION

The formulations of the invention comprise a suspension of a sanitizing composition, bacterial spores, and surfactants all contained in an aqueous solution. These formulations have the advantages of being a good surface cleaning agent and a good sanitizer along with providing the long term effect of beneficial bacteria that control pathogens and degrade wastes both on the surface and in the sewage system receiving the surface rinsate.

Sanitizing agents or composition and disinfectants belong to the same category of antimicrobial (active) ingredient. Antimicrobial (active) ingredient is a compound that kills microorganisms or prevents or inhibits their growth and reproduction and that contributes to the claimed effect of the product in which it is included. More specifically, sanitizer is an agent that reduces the number of microbial contaminants or pathogens to safe levels as judged by public health requirements as supported by Seymour S. Block, *Disinfection, Sterilization and Preservation,* 2nd Edition, 1977, pp 1025 and 1028; and Kirk-Other, "*Encyclopedia of Chemcial Technology*", 3rd Edition, 1977, pg. 794, which are incorporated herein by reference.

The surfactant component functions to clean the surface by removing the soil, dirt, dried urine and soap and helps in sanitizing the surface. The sanitizing composition sanitizes the surface (ills pathogens) and preserves the formulation from contamination by unwanted microorganisms. The bacterial spores, and vegetative cells therefrom, function to seed the waste collection system, control odor and provide a healthy dominant microbial population that inhibits the growth of pathogens through substrate competition, production of antibiotics, etc.

In one embodiment of the present invention, it has been found that a unique sanitizing composition formulated of 1,2-benzisothiazolin-3-one (Proxel), tetrasodium ethylenediaminetetraacetate (EDTA), and isopropyl alcohol (IPA) at a selected range of concentrations, combined with other components of the formula, can effectively inactivate indicator organisms. In addition, this sanitizing composition does not inactivate bacterial spores used in the formula even after a long period of contact. Different from most of the existing sanitizing products, this sanitizing composition is at neutral pH and does not contain chlorine-related materials, which are commonly used as sanitizers. Consequently, this sanitizing composition is more environmentally friendly and less or not corrosive. The sanitizing component of the invention in combination with selected bacterial spores functions to provide unique formulations unavailable in the art.

Tests have shown that the use of microorganisms selected by this invention can reduce the growth of an indicator organism, suggesting that maintaining a beneficial microbial population on a surface and in wastewater collection and treatment systems prevents multiplication of potential pathogens. The introduction of this mechanism into a surface cleaning product is another unique aspect of the present invention.

BRIEF DESCRIPTION OF THE DRAWINGS

For a fuller understanding of the nature and objects of the invention, reference should be made to the following detailed description of a preferred embodiment of practicing the invention, read in connection with the accompanying drawings, in which.

*licheniformis, Bacillus subtilis,* and *Bacillus polymyxa* from the present invention.

Figure 4:
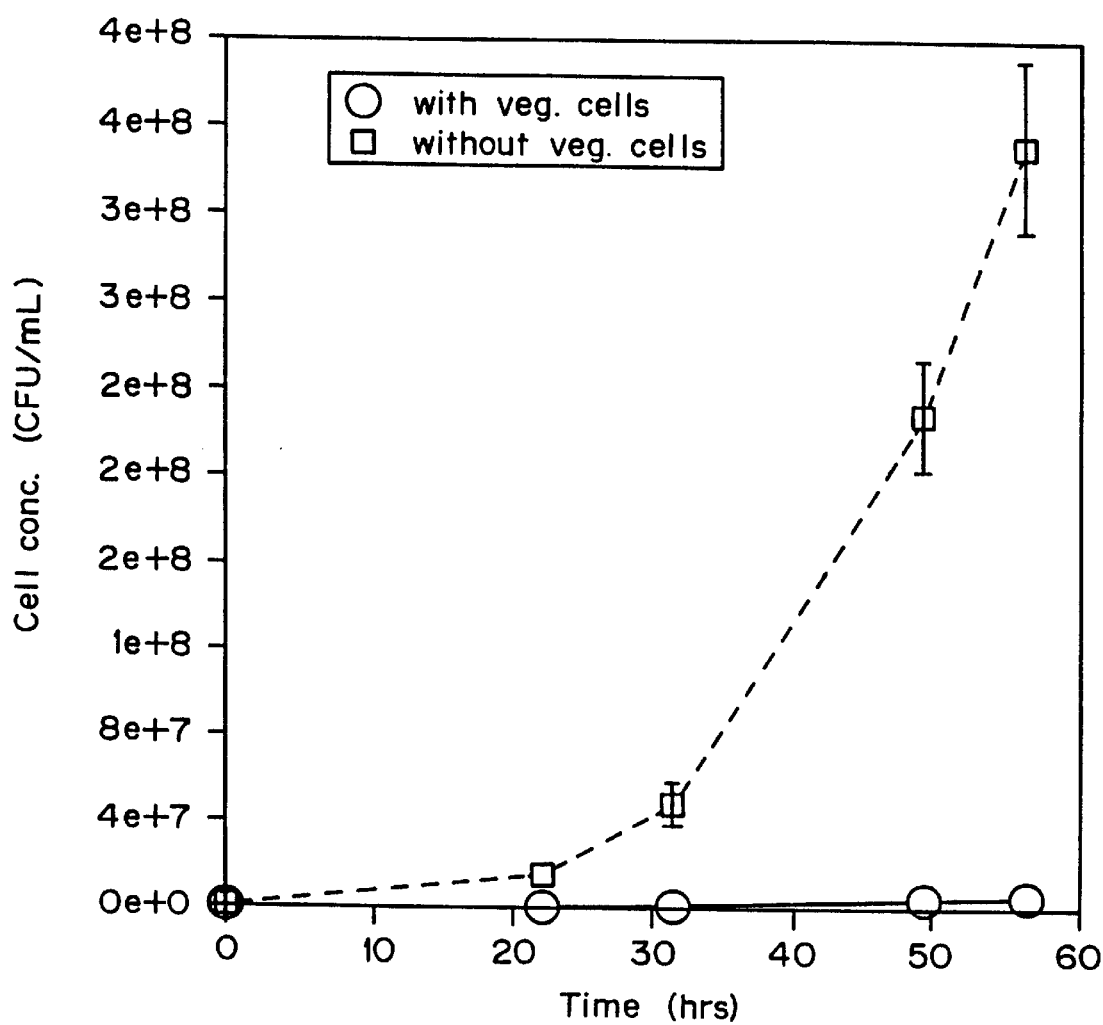

FIG. 4 illustrates growth of an indicator organism with and without exposure to vegetative cells of mixed *Bacillus amyloliquefaciens, Bacillus pasteurii,* and *Bacillus laevolacticus* from the present invention.

DETAILED DESCRIPTION OF THE INVENTION

When the formula of the invention is applied in use to a bathroom fixture, sink, toilet bowl, etc., it can be sprayed or squeezed out of a container directly onto a surface or brush. The formula is then left on the surface or scoured against the surface with a brush for not less than 10 minutes. The product is then flushed or rinsed with water and discharged from the fixture.

The formulas of the invention contain sanitizing agents, bacterial spores, and surfactants. Fragrance and dye are also added to control smell and color of the formulations, respectively. Depending on the intended use, the formula can optionally contain an abrasive. While the key components remain the same, different thickening agents might be used in the formulation with and without an abrasive.

The following is a basic description of the key components which make up formulations of the present invention:

Sanitizing Composition

Although many sanitizing agents can be used for inactivating pathogens on surfaces, not all of them can be used in the present invention. This is because the sanitizing agents used in this invention are not only required to inactivate pathogens effectively, but must not have negative effects on the stability and activity of the bacterial spores contained in the formulation. In addition, the sanitizing agents are required to be relatively friendly to the environment, and should not cause skin sensitization, and should not corrode the construction materials of the fixtures on which they are used.

A unique preferred sanitizing composition which achieves the above objective is composed of Proxel, EDTA, and IPA at selected ranges of concentrations. The maximum concentration of Proxel not likely to cause skin sensitization is about 2,900 mg/L. As shown in Tables 1 and 2, the suitable concentration ranges of Proxel, Versene (Versene contains 39% EDTA), and IPA for producing a 4 log reduction in the count of an indicator organism in 10 minutes are 0.087 to 0.29% (vol.), 0.36 to 1.19% (vol.), and 3.5 to 7% (vol.), respectively. An additional compound, methyl anthranilate, has also been used in the formulations of the invention. The purpose of using methyl antranilate is to assist in preservation of the formulations.

TABLE 1

Effect of Proxel and Versene
Concentrations on Inactivation of *P. aeruginosa* PRD10[1,2,3]

| Proxel Conc. (% v) | 0 | 0.087 | 0.17 | 0.23 | 0.29 |
|---|---|---|---|---|---|
| Versene Conc. (% v) | 0 | 0.36 | 0.70 | 0.95 | 1.19 |
| IPA Conc. (% v) | 5.25 | 5.25 | 5.25 | 5.25 | 5.25 |
| $Log_{10}$ Reduction in CFU/mL, 10 min | 1 | >4 | >4 | >4 | >4 |

[1]PRD 10 count in the control sample (using saline solution in the place of the formula) was $10^5$ CFU/mL.
[2]Data are means of triplicate samples.
[3]For the detailed test procedure, see Example 2.

TABLE 2

Effect of Isopropyl Alcohol Concentrations
on Inactivation of *P. aeruginosa* PRD10[1,2,3]

| IPA Conc. (% v) | 0 | 3.5 | 7.0 |
|---|---|---|---|
| Proxel Conc. (% v) | 0.29 | 0.29 | 0.29 |
| Versene Conc. (% v) | 1.19 | 1.19 | 1.19 |
| $Log_{10}$ Reduction in CFU/mL, 10 min | 2 | 4 | >4 |

[1]PRD 10 count in the control sample (using saline solution in the place of the formula) was $10^5$ CFU/mL.
[2]Data are means of triplicate samples.
[3]For the detailed test procedure, see Example 2.

Other sanitizing agents, such as quaternary ammonium compounds (QACs), nitro-containing organosulfur and sulfur-nitrogen compounds, may also be used in the formulation of this invention.

The public health requirements for a sanitizer are developed by various organizations, including EPA, USDA, and FDA. The requirements vary depending on applications of sanitizers and the product claims. A typical industry recognized criterion is that a sanitizer for inanimate, non-food contact surfaces must show a bacterial (indicator organism) reduction of at least 99.9% (i.e., 1,000 time reduction) within a practical contact time (e.g., less than 10 minutes). The efficacy claims made for a sanitizer product (killing rate, contact time) are required to be consistent with the supporting data. The sanitizing efficacy of the formula of the present invention is consistent with the greater than 1,000 times reduction rate described above as shown by the data in Table 6 on page 14 of the application for four gram negative indicator organisms.

Microorganisms

Any viable non-pathogenic microorganisms, or mixture thereof, capable of surviving the formulation and the intended use environment, and which have the ability to degrade or promote the degradation of lipids, proteins and carbohydrates common to domestic, institutional, and industrial sewage may be used in the present invention. In addition to having the capabilities and properties mentioned above, microorganisms capable of producing antibiotics are desirable.

Suitable types of microorganisms would principally include spore formers, such as the genus Bacillus. The genus Bacillus is preferred because these microorganisms not only have excellent waste degrading capabilities but also produce a protected spore form. Moreover, some Bacillus strains can produce antibiotics. Preferred bacteria include several strains of Bacillus developed by Sybron Chemicals, Inc. specifically adapted for high production of extracellular enzymes, particularly proteases, amylases, and lipases. These preferred strains include *Bacillus licheniformis* Culture DA 33 (ATCC 55406), *Bacillus subtilis* Culture 300 (ATCC 55405), and *Bacillus polymyxa* Culture polymyxa (ATCC 55407), *Bacillus amyloliquefaciens* Culture SB 1002*, *Bacillus pasteurii* Culture SB 1003*, and *Bacillus laevolacticus* Culture SB 1006*. The identification of the latter three strains is based on the BioLog data as shown in Table 3.

TABLE 3

BioLog Data for Identification of *Bacillus amyloliquefaciens* SB 1002, *Bacillus pasteurii* SB 1003, and *Bacillus laevolacticus* SB 1006

| Strain | BioLog ID | Version | Similarity Coefficient | Distance Coefficient |
|---|---|---|---|---|
| SB 1002 | *Bacillus amyloliquefaciens* | 3.7 | 0.668 | 4.092 |
| SB 1003 | *Bacillus pasteurii* | 3.5 | 0.727 | 3.976 |
| SB 1006 | *Bacillus laevolacticus* | 3.7 | 0.564 | 2.318 |

The following is a list of other bacterial strains available from American Type Culture Collection (ATCC), with their respective ATCC designation, which are suitable for use in the formulation of the present invention.

| *Bacillus licheniformis:* | *Bacillus amyloliquefaciens:* |
|---|---|
| 21417 | 23842 |
| 21424 | 23843 |
| 27811 | 23844 |
| 39326 | 23845 |

| *Bacillus subtilis:* | *Bacillus pasteurii:* |
|---|---|
| 6051a | 6452 |
| 21228 | 6453 |
| 21331 | 11859 |
| 35854 | |

| *Bacillus polymyxa:* | *Bacillus laevolacticus:* |
|---|---|
| 10401 | 23492 |
| 12060 | |
| 21551 | |
| 21993 | |

A suitable concentration level of viable microorganisms is about $10^7$ CFU/ml (CFU, colony forming unit) of the formulation. An operable concentration range for the microorganisms is from $1 \times 10^5$ to $1 \times 10^9$ CFU/ml.

Surfactants

Surfactants are also an essential component in the formulation of the present invention. The surfactants can wet and emulsify soil, including dirt, dried urine, soap, etc., present on a dirty surface. In addition, surfactants aid in the sanitization of the surface. Unlike surfactants usually used for surface cleaning, the surfactants used in the present invention have low toxicity for the microorganisms contained within the formulation. A single surfactant or a blend of several surfactants can be used.

Nonionic surfactants are generally preferred for use in the compositions of the present invention since they provide the desired wetting and emulsification actions and do not significantly inhibit spore stability and activity. Nonionic surfactants are surfactants having no electrical charge when dissolved or dispersed in an aqueous medium. Preferred nonionic surfactants used in this invention include aliphatic alcohol alkoxylates, polyalkylene oxide copolymers, alkyl phenol alkoxylates, carboxylic acid esters, carboxylic amides, and others.

Anionic surfactants or mixtures of anionic and nonionic surfactants may also be used in the formulations of the invention. Anionic surfactants are surfactants having a hydrophilic moiety in an anionic or negatively charged state in aqueous solution. Commonly available anionic surfactants include sulfonic acids, sulfuric acid esters, carboxylic acids, and salts thereof.

Abrasives, Thickening Agents, Fragrance, and Dyes

Abrasives are water-insoluble solid particles. The purpose of using abrasives is to provide deep scouring and cleaning. Depending on the application, abrasives may be optionally used in the formulation of the invention. Suitable abrasives include calcium carbonate, magnesium carbonate, silica, etc. The preferred particle size of the abrasive ranges from about 90 to 325 mesh.

Since the specific gravity of bacterial spores is usually higher than that of water, a thickening agent needs to be used in this invention to suspend the spores. Suitable aqueous thickening agents include: polyacrylic acid, polystyrene, polyvinyl alcohol, polypropylene, etc. A preferred thickening agent for suspending bacterial spores is polyacrylic acid (e.g., Acrysol TT615 from Rohm and Haas Co.). If an abrasive is used in the formulation, thickening agents in addition to polyacrylic acid might be needed to maintain the suspension of the abrasive. Tests show that an inorganic clay, Laponite, from Southern Clay Corporation, is suitable for this purpose.

A fragrance and a dye can be optionally added to mask the odor and to control the color of the product components, respectively, and for market appeal. The fragrance and dye must be compatible with the other components of the formulation.

The formulas in this invention can typically have the following ingredients (Table 4 and 5):

TABLE 4

Typical Formulation of the Invention Containing an Abrasive

| | Broad | Preferred |
|---|---|---|
| Sanitizing agents | 3–9% w | 5–7% w |
| Bacterial spores | $1\times10^5$–$1\times10^9$ CFU/ml | $1\times10^6$–$1\times10^8$ CFU/ml |
| Surfactants | 2–7% w | 3–5% w |
| Abrasive | 0.01–4% w | 2–3% w |
| Thickening Agent | 0.2–3% w | 1–2% w |
| Fragrance | 0.1–0.6% w | 0.2–0.4% w |
| Dye | 0.0006–0.003% w | 0.001–0.002% w |
| Water | Balance | Balance |

TABLE 5

Typical Formulation of the Invention Containing No Abrasive

| | Broad | Preferred |
|---|---|---|
| Sanitizing agents | 3–9% w | 5–7% w |
| Bacterial spores | $1\times10^5$–$1\times10^9$ CFU/ml | $1\times10^6$–$1\times10^8$ CFU/ml |
| Surfactants | 2–7% w | 3–5% w |
| Thickening Agent | 0.2–3% w | 1–2% w |
| Fragrance | 0.1–0.6% w | 0.2–0.4% w |
| Dye | 0.0006–0.003% w | 0.001–0.002% w |
| Water | Balance | Balance |

The invention is further illustrated by the following examples which constitute preferred embodiments of the invention.

EXAMPLE 1

The following illustrates the preparation of a surface cleaning and sanitizing formula of the present invention.

A. Preparation of the spore mixture

Into 1 gallon tap water were added the following nutrients:

0.04 lbs yeast extract 0.08 lbs corn syrup solids 0.016 lbs ammonium chloride 0.0035 lbs disodium phosphate
0.00086 lbs monosodium phosphate
0.00066 lbs calcium chloride dihydrate
0.0016 lbs magnesium sulfate
0.00066 lbs manganese sulfate
0.63 ml anti-foam The water mixture was then sterilized for 30 minutes at 15 pounds pressure and 250° F. The water mixture was cooled and inoculated with *Bacillus subtilis* Culture 300. The bacteria were allowed to grow for 60 to 65 hours with aeration at 88° F. and to form spores (concentration of spores should be about $1 \times 10^9$ CFU/ml).

The above procedure was separately repeated for *Bacillus licheniformis* Culture DA 33 and *Bacillus polymyxa* Culture polymyxa, respectively, resulting in three separate bacterial spore suspensions.

A spore mixture of these three stains was made from the above three suspensions in a ratio by count of 90% *Bacillus licheniformis* Culture DA 33, 5% *Bacillus subtilis* Culture 300, and 5% *Bacillus polymyxa* Culture polymyxa.

B. Procedure for preparing the formula

The following components were added to 3,000 ml of tap water under agitation:

0.000026 lbs methyl anthranilate
0.017 lbs Proxel GXL
0.076 lbs Versene
0.17 lbs Trycol 5940
0.10 lbs Polytergent SL62
0.49 lbs isopropyl alcohol (70%)
0.036 lbs Herbal fragrance
0.00015 lbs Liquitint SS Blue
0.0007 lbs Silica 160
0.18 lbs Acrysol TT 615

Bacterial spore mixture made as described above was added to the 3,000 ml solution of the formula to a total count of ca. $6 \times 10^7$ CFU/ml in the finished formula. The final volume was adjusted to 3,785 ml (1 gallon) with tap water and the final pH to 7 to 8 using a 50% sodium hydroxide solution.

EXAMPLE 2

Five g beef extract (Difco), 5 g NaCl, and 10 g peptone (Difco) were boiled in 1 liter distilled water for 20 minutes. This nutrient broth was then filtered through filter paper, placed in 10 ml portion in 20×150 mm test tubes, and autoclaved for 20 minutes at 121° C. This broth was used to grow each of the following five indicator microorganisms: *Pseudomonas aeruginosa* PRD 10 (ATCC 15442), *Escherichia coli* ATCC 61489, *Salmonella cholerasius* ATCC 10708, *Salmonella typhi* ATCC 6539, and *Staphylococcus aureus* FDA 209. The *P. aeruginosa* PRD 10 culture was grown for 48 to 54 hours and the other four strains were grown for about 24 hours, both at 35° C. and without agitation.

A sterile glass cover slip (Thomas Scientific, #6662-F43) was placed in each well of a cell culture plate (12-well, VWR, #62408-597). 0.02 ml of the *P. aeruginosa* culture suspension was added onto the surface of the glass slip and allowed to be air dried for 1.5 to 2.5 hours in a laminar hood at room temperature. The contaminated area on the glass slip was then covered with 0.04 ml of the formula prepared by Example 1 set forth above. After 10 minutes of contact at 23° C., 1.1 ml of sterile saline solution (0.85% NaCl) containing 0.05% Tween 80 was added to each well to dilute the sample and elute the bacteria from the glass slip. The eluant was serially diluted with a phosphate buffer solution. 0.1 ml of the dilution containing the eluant was plated on each MacConkey agar plate. The agar plates were incubated for ca. 24 hours at 35° C. and the colonies on each plate were counted. Simultaneously, a control experiment (using the saline solution in the place of the formula) was also performed.

The same procedure for sanitization test illustrated above was also used to test sanitizing efficacy of the formula against *Escherichia coli* ATCC 61489, *Salmonella cholerasius* ATCC 10708, and *Salmonella typhi* ATCC 6539.

A similar sanitization test procedure was also used to examine a formula sample containing no spores against *Staphylococcus aureus* FDA 209. Since both the Staphylococcus strain and the Bacillus strains are Gram positive, the use of the formula sample without spores could eliminate the interference of the spores on the sanitization test. In this test, 0.1 ml of the dilution containing the eluant was plated on Mannitol salt agar, instead of MacConkey agar, to obtain the Staphylococcus counts.

The test results for sanitizing efficacy of the formula prepared by Example 1 are shown in Table 6. Sanitization test data using a 1.25% phenol solution as the sanitizing agent (positive control) are also shown. The results indicate that the formula can effectively inactivate the five indicator microorganisms, with a higher efficacy against the Gram negative microbes (*Pseudomonas aeruginosa* PRD 10, *Escherichia coli* ATCC 61489, *Salmonella cholerasius* ATCC 10708, and *Salmonella typhi* ATCC 6539) than against the Gram positive strain (*Staphylococcus aureus* FDA 209).

TABLE 6

Sanitizing Efficacy of the Formula on Five Indicator Organisms

| Treatment | Bacterial count after 10-min. contact* (CFU/mL) | | | | |
|---|---|---|---|---|---|
| | *P. aeruginosa* PRD 10 | *E. coli* ATCC 61489 | *S. scolerasuis* ATCC 10708 | *S. typhi* ATCC 6539 | *S. aureus* FDA 209 |
| Saline solution (control) | $(1.0 \pm 0.2) \times 10^5$ | $(3.0 \pm 0.6) \times 10^5$ | $(4.2 \pm 3.9) \times 10^5$ | $(2.9 \pm 0.9) \times 10^4$ | $(1.2 \pm 0.2) \times 10^5$ |
| Phenol solution (1.25%) | $<10^1$ | $<10^1$ | $(6.0 \pm 4.2) \times 10^2$ | $<10^1$ | $(3.3 \pm 0.1) \times 10^1$ |
| Formula | $<10^1$ | $<10^1$ | $(6.0 \pm 5.7) \times 10^1$ | $<10^1$ | $(2.3 \pm 1.9) \times 10^{4**}$ |

*Data are means of triplicate samples plus standard deviation.
**Formula containing no spores

EXAMPLE 3

The formula sample containing no spores as used in Example 2 set forth above was also tested for its capability to inhibit the growth of mildews. A fungal strain, *Aspergillus niger*, was grown on potato dextrose agar plates for 4 days at 30° C. and formed spores. 5 ml of sterile 0.05% Tween 80 solution was used to elute the fungal spores from the agar plates. This spore suspension was then mixed with 95 ml of potato dextrose agar solution at about 55° C. and placed in 10 ml portion in Petri dishes. The agar plates were solidified at room temperature. 0.03 ml of the formula sample containing no spores was added into a 0.25 inch sterile concentration disc (Difco) in a Petri dish and the disc was placed onto each of the solidified agar plates, along with two discs absorbing 0.03 ml of 1.25% phenol and distilled water, respectively. The agar plates were then incubated for ca. 24 hours at 30° C. and the inhibition zone on each plate was measured. As shown in Table 7, the formula could significantly inhibit the growth of the Aspergillus strain.

TABLE 7

Inhibition of *Aspergillus niger* Growth by the Formula

| Treatment | Formula | 1.25% Phenol | Distilled Water |
|---|---|---|---|
| Diameter of inhibition zone* (mm) | 8.3 ± 0.3 | 13 ± 0 | 0 ± 0 |

*Data are the means of triplicate samples plus standard deviation.

EXAMPLE 4

Two samples of the formula containing spores made by Example 1 set forth above were stored at 23° C. and 35° C., respectively. 0.04 ml aliquots were removed from each stored sample on day 1, day 31, and day 74. The procedure listed in Example 2 was used to test the sanitizing efficacy of the stored formula over time. As shown in Table 8, the formula could inactivate *P. aeruginosa* PRD 10 by greater than a factor of $1 \times 10^3$ (3 log) after 74 days storage at either 23° C. or 35° C., indicating that the sanitizing efficacy of the formula does not change during storage.

TABLE 8

Shelf-Stability of the Formula:
Sanitizing Effect on *P. aeruginosa* PRD 10

| | *P. aeruginosa* count after 10-min. contact* (CFU/mL) | | |
|---|---|---|---|
| Treatment | Day 1 | Day 31 | Day 74 |
| Saline solution (control) | $(1.0 \pm 0.2) \times 10^5$ | $(2.2 \pm 1.4) \times 10^5$ | $(1.0 \pm 0.3) \times 10^5$ |
| Formula stored at 23° C. | $<10^1$ | $<10^1$ | $(1.7 \pm 1.5) \times 10^2$ |
| Formula stored at 35° C. | $<10^1$ | $(2.3 \pm 1.5) \times 10^2$ | $<10^1$ |

*Data are means of triplicate samples plus standard deviation.

Figure 1:
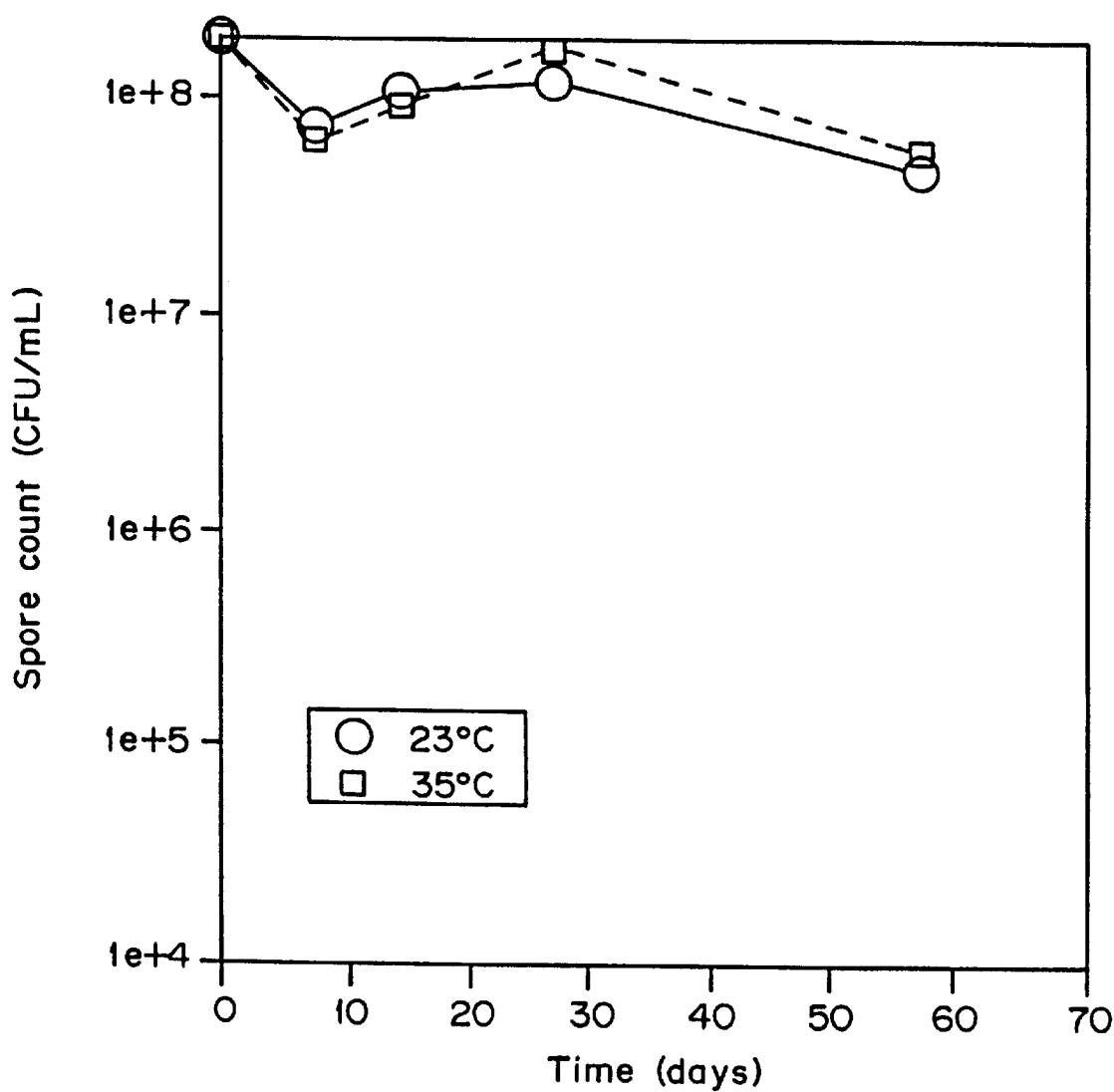
FIG. 1 illustrates a plot of spore shelf stability at two different temperatures.

One ml of each formula sample stored at 23° C. or 35° C. was also removed on day 1, 7, 14, 27, and 57, respectively. The sample was serially diluted with a phosphate buffer solution and the dilution, contained in a test tube, was immersed in a 80° C. oil bath for 10 minutes. The dilution was then cooled to room temperature in a beaker of distilled water. 0.1 ml of this dilution was plated on each of duplicate standard method agar plates for spore count. The agar plates were incubated for ca. 24 hours at 35° C. and the colonies counted. The test results are shown in FIG. 1 of the drawings. These data demonstrate that the spore count in the formula is stable during the storage at 23° C. and 35° C.

EXAMPLE 5

Figure 2:
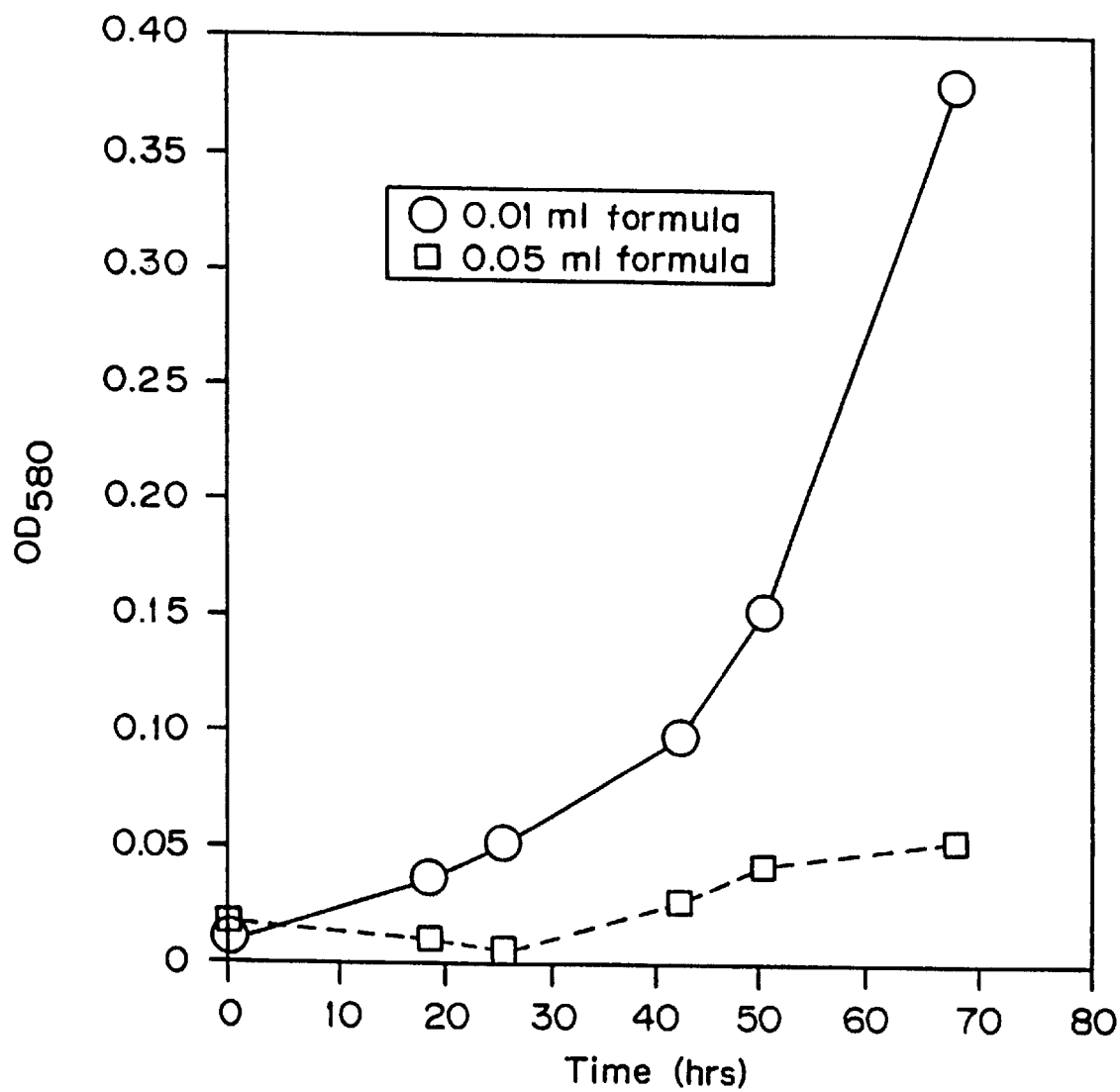
FIG. 2 illustrates a plot of spore germination and growth after dilution.

Different volumes of the formula containing spores made by Example 1 set forth above were added into test tubes, each of which contained 10 ml of plate count broth. The samples were incubated at 23° C. without agitation. When 0.01 ml of the formula sample was added into 10 ml of plate count broth, the spores in the formula germinated (see FIG. 2), as illustrated by the increase in optical density. These data demonstrate that the spores in the formula are capable of germinating and growing after dilution and under suitable nutrient conditions.

EXAMPLE 6

Figure 3:
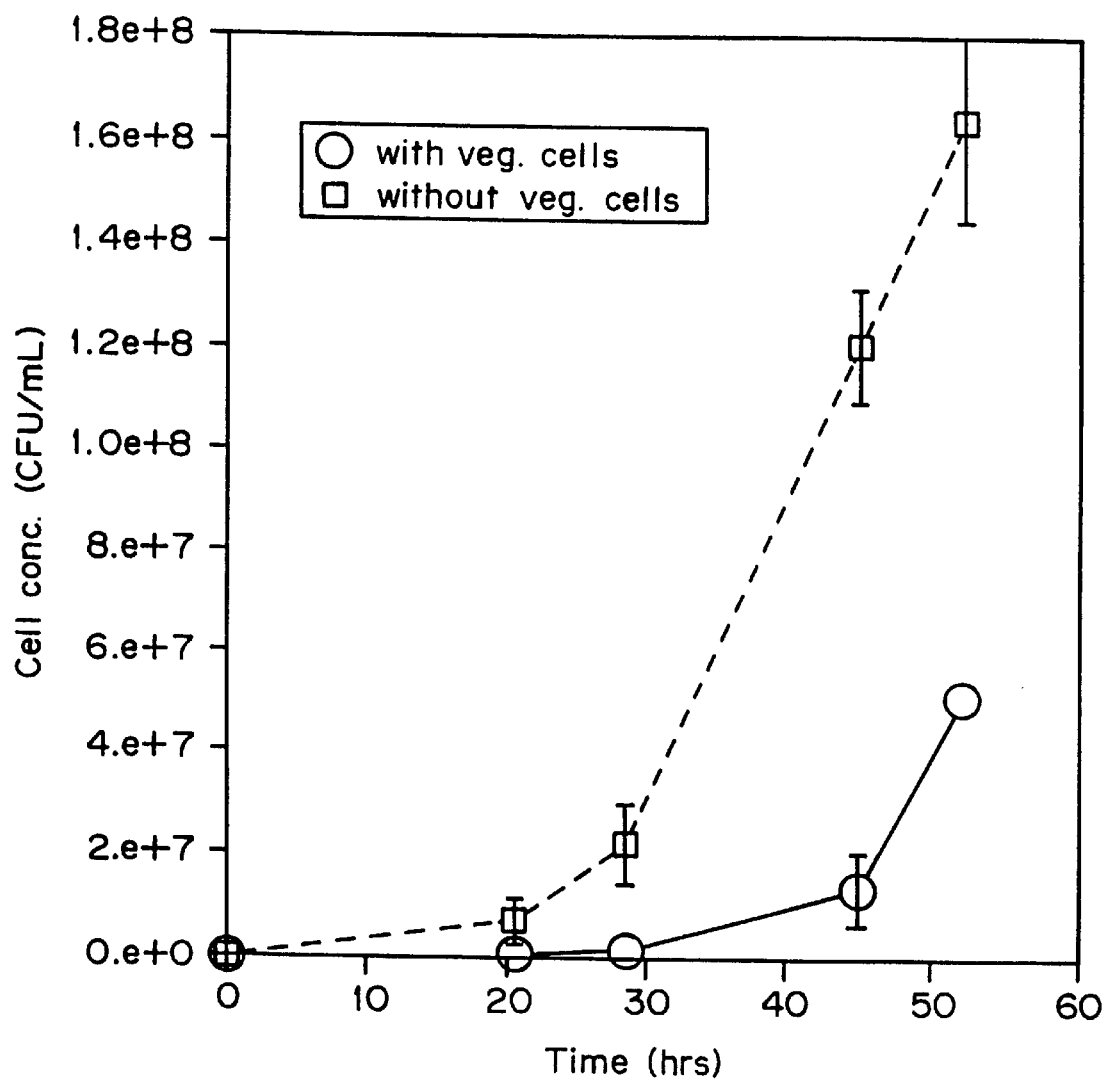
FIG. 3 illustrates growth of an indicator organism with and without exposure to vegetative cells of mixed *Bacillus*

A suspension of the spore mixture as used in Example 1 was added to 10 ml of plate count broth. The culture was incubated at 35° C. without agitation. After 24 hours, the spores in the culture germinated to vegetative cells. In addition, a *P. aeruginosa* PRD 10 suspension was grown as described in Example 2 and diluted by 100 times with a phosphate buffer solution. Two culture samples were then prepared as follows: 1) 1 ml of vegetative cell suspension from the mixed spore culture and 0.1 ml of the diluted *P. aeruginosa* PRD 10 suspension were added to 14 ml of 1/10 diluted plate count broth, and 2) 0.1 ml of the diluted *P. aeruginosa* PRD 10 suspension was added to 15 ml of 1/10 diluted plate count broth. These two samples were incubated at 23° C. without agitation. Aliquots were removed from each culture sample over time for plate counts on MacConkey agar. The growth of the *P. aeruginosa* PRD 10 was inhibited or decreased by the mixed culture of the spore-forming species, as compared to the culture containing only *P. aeruginosa* PRD 10 (FIG. 3). This result suggests that maintaining an exogenous microbial population (e.g., the Bacillus strains) could prevent multiplication of unwanted organisms (e.g., pathogens) on the same location.

Beneficial microbes can compete with unwanted organisms for a common factor, such as food, light, space, etc. (J. E. Bailey and D. F. Ollis, *Biochemical Engineering Fundamentals,* 2nd Edition, Chapter 13, p. 854–900, McGraw-Hill Publishing Co., 1986). Factors affecting this competitive process include nutrient utilization rate, cell growth rate, and concentration ratio of competing species. By both employing suitable non-pathogenic spore-forming strains and controlling the spore concentration, the present invention can provide a biocontrol mechanism that prevents or reduces pathogen multiplication on surfaces and in wastewater or sewage collection and treatment systems.

EXAMPLE 7

An additional spore mixture of three strains, *Bacillus amyloliquefaciens* Culture SB 1002, *Bacillus pasteurii* Culture SB 1003, and *Bacillus laevolacticus* Culture 1006, was prepared as in Example 1 and in a ratio by count of 1/3 for each strain. This spore mixture was then used to replace the spore mixture consisting of *Bacillus licheniformis* Culture DA 33, *Bacillus subtilis* Culture 300, and *Bacillus polymyxa* Culture polymyxa, which was used in Examples 1 to 6, to prepare the formula of this invention. Tests have shown that the spore count of mixed *Bacillus amyloliquefaciens* Culture SB 1002, *Bacillus pasteurii* Culture SB 1003, and *Bacillus laevolacticus* Culture 1006 is stable in the formula during the storage at 23° and 35° C. In addition, these spores germinated and grew when 0.01 ml of the formula sample was added into 10 ml of plate count broth.

The indicator organism, *Pseudomonas aeruginosa* PRD 10, was grown with and without the vegetative cells of mixed *Bacillus amyloliquefaciens* Culture SB 1002, *Bacillus pasteurii* Culture SB 1003, and *Bacillus laevolacticus* Culture 1006 following the procedure listed in Example 6. Similar to the result found in Example 6, the growth of *Pseudomonas aeruginosa* PRD 10 was also inhibited by the mixed culture of *Bacillus amyloliquefaciens* Culture SB 1002, *Bacillus pasteurii* Culture SB 1003, and *Bacillus laevolacticus* Culture 1006 as shown by the data in FIG. 4.

While specific embodiments of the invention have been illustrated and described herein, it is realized that modifications and changes will occur to those skilled in the art. It is therefore to be understood that the appended claims are intended to cover all modifications and changes as fall within the true spirit and scope of the invention.

We claim:

1. A liquid cleaner and sanitizer formulation which comprises:

a sanitizing composition suitable for inactivating surface pathogens comprising isopropyl alcohol;

viable spore form of non-pathogenic microorganisms for: 1) preventing multiplication of pathogens; and 2) degrading organic wastes;

a surfactant or a blend of surfactants for cleaning surfaces;

all being contained in an aqueous medium having a pH of from about 6.0 to 9.0, and wherein said sanitizing composition and microorganisms are used in concentrations effective to inactivate pathogens and to induce beneficial microbial activity, respectively with said formulation being capable of reducing the four gram negative indicator organisms (*P. aeruginosa* PRD 10, *E. coli* ATCC 61489, *S. cholerasium* ATCC 10708, *S. typhi* ATCC 6539) by greater than 1000 times within 10 minutes.

2. The formulation of claim 1 which further includes an abrasive.

3. The formulation of claim 1 in which the sanitizing composition further comprises ethylenediaminetetraacetate and 1,2-benzisothiazolin-3-one.

4. The formulation of claim 1 in which said non-pathogenic microorganisms comprises a mixture of Bacillus strains.

5. A liquid cleaner and sanitizer formulation which comprises:

a sanitizing agent suitable for inactivating surface pathogens comprising 3.5 to 7% isopropyl alcohol;

viable non-pathogenic microorganisms, adapted for production of protease, amylase and lipase, in a concentration from about $1\times10^5$ CFU/ml to $1\times10^9$ CFU/ml and in the form of a single strain or a mixture of several strains of Bacillus that are common to domestic, industrial or institutional sewage;

a surfactant or a blend of several surfactants selected from the group consisting of aliphatic alcohol alkoxylates, polyalkylene oxide copolymers, alkyl phenol alkoxylates, carboxylic acid esters, carboxylic amides, sulfonic acid esters;

a thickening agent; and, a preservative which functions to inhibit or prevent the growth of microbial contaminants in the formulation;

all being contained in an aqueous medium having a pH of from about 6.0 to 9.0, and where the at least one strain of Bacillus is selected from the group consisting of *Bacillus licheniformis, Bacillus subtilis, Bacillus polymyxa, Bacillus amyloliquefaciens, Bacillus pasteurii,* and *Bacillus laevolacticus* having all the identifying characteristics of American Type Culture Collections deposit Nos. 55406, 55405 and 55407, and Sybron Nos. SB 1002, SB 1003, and SB 1006, respectively, or mutants thereof possessing all the identifying characteristics thereof with said formulation being capable of reducing four gram negative indicator organisms (*P. aeruginosa* PRD 10, *E. coli* ATCC 61489, *S. cholerasium* ATCC 10708, *S. typhi* ATCC 6539) by greater than 1000 times within 10 minutes.

6. The formulation of claim 5 in which the sanitizing composition further comprises ethylenediaminetetraacetate.

7. The formulation of claim 5 which further contains an abrasive.

8. A liquid cleaner and sanitizer formulation which comprises:

a sanitizing composition suitable for inactivating surface pathogens comprising isopropyl alcohol;

viable non-pathogenic microorganisms for preventing multiplication of pathogens and degrading organic wastes;

a surfactant or a blend of surfactants for cleaning surfaces;

a thickening agent or a blend of thickening agents; and, a preservative which functions to inhibit or prevent the growth of microbial contaminants in the formulation;

all being contained in an aqueous medium having a pH of from about 6.0 to 9.0, and wherein said sanitizing compositions and microorganisms are used in concentrations effective to inactivate pathogens and to induce beneficial microbial activity, respectively; and wherein said viable non-pathogenic microorganism(s) is at least one strain selected from the group consisting of *Bacillus subtilis, Bacillus lichenifonnis, Bacillus polymyxa, Bacillus amyloliquefaciens, Bacillus pasteurii,* and *Bacillus laevolacticus* with said formulation being capable of reducing four gram negative indicator organisms (*P. aeruginosa* PRD 10, *E. coli* ATCC 61489, *S. cholerasium* ATCC 10708, *S. typhi* ATCC 6539) by greater than 1000 times within 10 minutes.

9. The formulation of claim 8 in which the sanitizing composition further comprises ethylenediaminetetraacetate.

10. The formulation of claim 9 in which the microorganisms are present in a concentration of from about $1\times10^5$ CFU/ml to $1\times10^9$ CFU/ml.

* * * * *